(12) United States Patent
Coffin et al.

(10) Patent No.: US 11,304,851 B2
(45) Date of Patent: Apr. 19, 2022

(54) PUSH-TO-FIT EARPLUG WITH TIP CAVITY

(71) Applicant: 3M INNOVATIVE PROPERTIES COMPANY, St. Paul, MN (US)

(72) Inventors: Robert C. Coffin, Plainfield, IN (US); Matthew V. Stonebraker, Jr., Lafayette, IN (US); Jacob H. Ely, Carmel, IN (US); Jeff L. Hamer, Springville, IN (US); Kenneth F. Teeters, Zionsville, IN (US); Ravi Thomas, Avon, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 236 days.

(21) Appl. No.: 16/643,080

(22) PCT Filed: Aug. 30, 2018

(86) PCT No.: PCT/IB2018/056648
§ 371 (c)(1),
(2) Date: Feb. 28, 2020

(87) PCT Pub. No.: WO2019/043627
PCT Pub. Date: Mar. 7, 2019

(65) Prior Publication Data
US 2020/0197224 A1   Jun. 25, 2020

Related U.S. Application Data

(60) Provisional application No. 62/553,596, filed on Sep. 1, 2017.

(51) Int. Cl.
*A61F 11/08* (2006.01)

(52) U.S. Cl.
CPC ............. *A61F 11/08* (2013.01); *A61F 11/085* (2022.01); *A61F 2210/0071* (2013.01); *A61F 2240/001* (2013.01)

(58) Field of Classification Search
CPC .... A61F 11/06; A61F 11/08; A61F 2011/085; A61F 2210/0071; H04R 1/10;
(Continued)

(56) References Cited

U.S. PATENT DOCUMENTS

| 4,193,396 A | 3/1980 | Wacker |
| 4,253,452 A | 3/1981 | Powers |

(Continued)

FOREIGN PATENT DOCUMENTS

| CA | 2709768 | 12/2010 |
| CN | 103054670 | 4/2013 |

(Continued)

OTHER PUBLICATIONS

US 9,592,159 B2, 03/2017, Endle (withdrawn)
International Search Report for PCT International Application No. PCT/IB2018/056648, dated Dec. 21, 2018, 2 pages.

*Primary Examiner* — Camtu T Nguyen
(74) *Attorney, Agent, or Firm* — Katherine M. Scholz

(57) ABSTRACT

An earplug comprises a core and a sound-attenuating body attached to the core, the sound-attenuating body comprising a tip cavity extending proximally from the tip of the sound-attenuating body and comprising a distal opening. The tip cavity side wall includes a plurality of protrusions extending inwardly toward the longitudinal axis of the core. The plurality of protrusions may include from 2 to 12 protrusions. A method of making an earplug includes covering at least a portion of a core with a material including unactivated foaming agent; inserting an end of the core and at least a portion of the material into a mold cavity; and activating the foaming agent to create a sound-attenuating body. The sound-attenuating body has a base, tip, and tip cavity with a plurality of protrusions. The mold cavity may include a boss with a cup and plurality of cut-outs on the cup for forming the protrusions.

19 Claims, 9 Drawing Sheets

(58) Field of Classification Search
CPC .. H04R 1/1016; H04R 1/1058; H04R 1/1075; H04R 1/1083
See application file for complete search history.

(56) References Cited

U.S. PATENT DOCUMENTS

| | | | |
|---|---|---|---|
| 4,314,553 | A | 2/1982 | Westerdal |
| 4,481,158 | A | 11/1984 | Georlette |
| 4,555,313 | A | 11/1985 | Duchane |
| 5,249,309 | A | 10/1993 | Berg |
| 5,541,677 | A | 7/1996 | Huhtala |
| 5,581,821 | A | 12/1996 | Nakano |
| 5,668,354 | A | 9/1997 | Falco |
| 5,711,313 | A | 1/1998 | Fleming |
| 5,806,506 | A | 9/1998 | Kitamura |
| 5,811,742 | A | 9/1998 | Leight |
| 6,148,821 | A * | 11/2000 | Falco .............. H04R 1/1016 128/864 |
| 6,340,227 | B1 | 1/2002 | Solberg |
| 6,440,339 | B1 | 8/2002 | Magidson |
| D492,766 | S | 7/2004 | Falco |
| 6,938,622 | B2 | 9/2005 | Huang |
| 7,210,484 | B1 | 5/2007 | Tiemens |
| 7,264,081 | B2 | 9/2007 | Bruck |
| 7,984,716 | B2 | 7/2011 | Purcell |
| 8,118,031 | B2 | 2/2012 | Seville |
| 8,671,948 | B2 | 3/2014 | Turdjian |
| 8,679,607 | B2 | 3/2014 | Hamer |
| 8,968,613 | B2 | 3/2015 | Endle |
| 9,549,855 | B2 | 1/2017 | Hamer |
| 9,737,439 | B2 | 8/2017 | Endle |
| 2002/0124851 | A1 | 9/2002 | Knauer |
| 2003/0159878 | A1 | 8/2003 | Hakansson |
| 2004/0045558 | A1 | 3/2004 | Taylor |
| 2004/0079579 | A1 | 4/2004 | Barwacz |
| 2005/0056289 | A1 | 3/2005 | Jenkins, Jr. |
| 2005/0229938 | A1 | 10/2005 | Jenkins, Jr. |
| 2005/0230181 | A1 | 10/2005 | Woo |
| 2006/0175722 | A1* | 8/2006 | Babcock ............. B29C 44/0461 264/41 |
| 2007/0086599 | A1 | 4/2007 | Wilmink |
| 2007/0227546 | A1 | 10/2007 | Schumaier |
| 2009/0321176 | A1 | 12/2009 | Cartwright |
| 2012/0073583 | A1 | 3/2012 | Turdjian |
| 2012/0272974 | A1 | 11/2012 | Magidson |
| 2013/0014768 | A1 | 1/2013 | Vaarbroe |
| 2014/0014121 | A1* | 1/2014 | Endle ...................... C08J 9/105 128/867 |
| 2014/0097033 | A1 | 4/2014 | Fincham |
| 2014/0230830 | A1 | 8/2014 | Hamer |
| 2014/0305733 | A1 | 10/2014 | Leight |
| 2015/0059776 | A1* | 3/2015 | Hung ..................... A61F 11/08 128/867 |
| 2015/0335489 | A1* | 11/2015 | Hamer ................... A61F 11/08 128/864 |
| 2015/0335490 | A1 | 11/2015 | Hamer |
| 2017/0079845 | A1 | 3/2017 | Cai |

FOREIGN PATENT DOCUMENTS

| | | |
|---|---|---|
| CN | 203183139 | 9/2013 |
| JP | 2009200670 | 9/2009 |
| JP | 2012075850 | 4/2012 |
| NL | 9401212 | 3/1996 |
| TW | M304038 | 1/2007 |
| TW | M497521 | 3/2015 |
| WO | WO 2003-063744 | 8/2003 |
| WO | WO 2004-100608 | 11/2004 |
| WO | WO 2005-120131 | 12/2005 |
| WO | WO 2009-020644 | 2/2009 |
| WO | WO 2010-138447 | 12/2010 |
| WO | WO 2019-043625 | 3/2019 |
| WO | WO 2019-043626 | 3/2019 |

\* cited by examiner

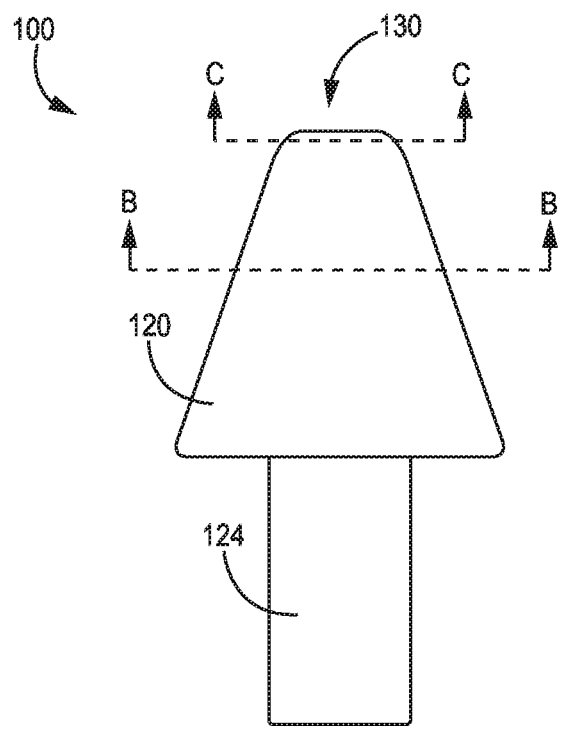
FIG. 5A
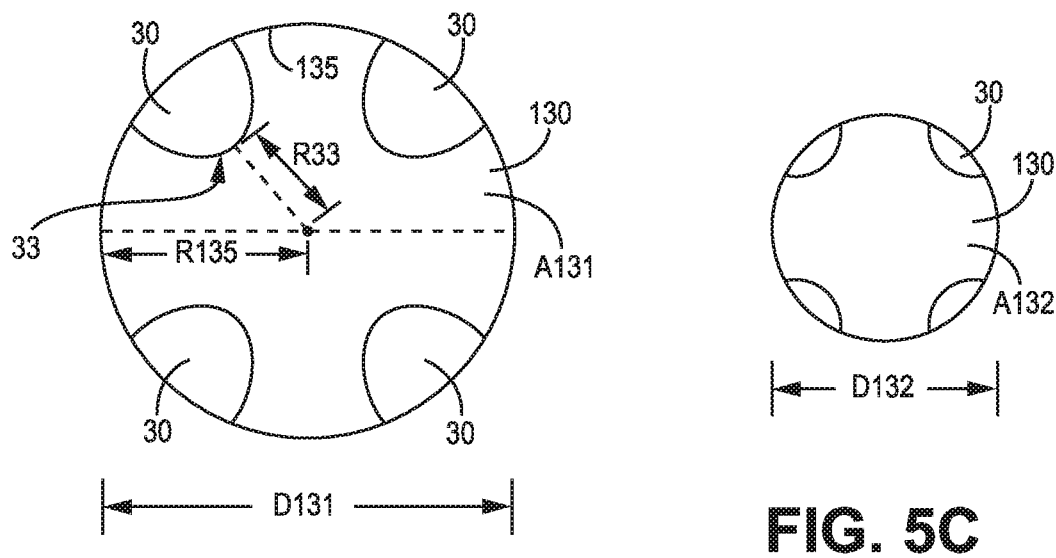
FIG. 5B
FIG. 5C

PUSH-TO-FIT EARPLUG WITH TIP CAVITY

CROSS REFERENCE TO RELATED APPLICATIONS

This application is a national stage filing under 35 U.S.C. 371 of PCT/IB2018/056648, filed Aug. 30, 2018, which claims the benefit of U.S. Provisional Application No. 62/553,596, filed Sep. 1, 2017, the disclosure of which is incorporated by reference in its/their entirety herein.

The present disclosure relates to hearing protection devices, e.g., push-to-fit earplugs, and methods of manufacturing the hearing protection devices.

The use of hearing protective and noise attenuating devices is well known, and various types of devices have been considered. Such devices include earplugs and semi-aural devices partially or completely constructed of foam or rubber materials that are inserted into, or placed over, the ear canal of a user to physically obstruct the passage of sound waves into the inner ear.

Compressible or "roll-down" type earplugs generally comprise a compressible, resilient body portion and may be made of suitable slow recovery foam materials. The earplug may be inserted into the ear canal of a user by first rolling it between fingers to compress the body portion, then pushing the body portion into the ear canal, and subsequently allowing the body portion to expand to fill the ear canal.

Push-to-fit type earplugs have also been considered, and may include a compressible attenuating portion and a stiff portion (e.g., a stem) that extends from the attenuating portion. To insert a push-to-fit type earplug, the user grasps the stiff portion and pushes the attenuating portion into the ear canal with an appropriate level of force. The attenuating portion compresses as it is accommodated in the ear canal. Push-to-fit earplugs may allow the earplug to be quickly and easily inserted in an ear canal, and may promote hygiene by minimizing contact with the attenuating portion of the earplug prior to insertion.

SUMMARY

Hearing protection devices, e.g., push-to-fit earplugs, having a tip cavity in the sound-attenuating body and methods of manufacturing the hearing protection devices are described herein.

The tip cavities in the earplugs according to an embodiment may, in one or more embodiments, provide a volume into which the surrounding material of the sound-attenuating body can collapse as the earplug is advanced into an ear canal and/or is resident therein. This feature may, in one or more embodiments, make insertion of the earplugs easier and/or improve comfort, particularly for users with smaller ear canals.

In addition to providing a volume for the material of the sound-attenuating body to occupy, the end of a core located in the earplug may be recessed into the tip cavity, which may, in one or more embodiments, reduce the likelihood that a user will feel the end of the core as the sound-attenuating body is inserted into and/or resident within an ear canal. Although the end of the core is recessed within the tip cavity, it may, in one or more embodiments, extend into the tip cavity such that the end of the core is located above the bottom of the tip cavity according to an embodiment.

According to an embodiment, the earplug comprises a core comprising a proximal end, a distal end, and a major outer surface and a longitudinal axis extending from the proximal end to the distal end; a sound-attenuating body attached to the major outer surface of the core, the sound-attenuating body comprising a base and a tip, the distal end of the core disposed within the sound-attenuating body and the tip extending distally beyond the distal end of the core; and a tip cavity of the sound-attenuating body extending proximally from the tip and comprising a distal opening, the tip cavity having a volume defined by a side wall formed by the sound-attenuating body and a bottom at least partially formed by the distal end of the core. The tip cavity side wall comprises a plurality of protrusions extending inwardly toward the longitudinal axis. The plurality of protrusions may include from 2 to 12 protrusions. In some embodiments, each of the of protrusions has a proximal end that contacts the distal end of the core.

According to an embodiment, a method of making an earplug comprises covering at least a portion of a major outer surface of a core that comprises a first material with a second material that comprises an unactivated foaming agent, the core comprising a proximal end, a distal end, and a major outer surface and a longitudinal axis extending from the proximal end to the distal end; inserting the distal end of the core and at least a portion of the second material into a mold cavity; and activating the unactivated foaming agent in the mold cavity to form a sound-attenuating body in the mold cavity that is attached to the major outer surface of the core. The sound-attenuating body comprises a base and a tip, the distal end of the core disposed within the sound-attenuating body and the tip extending distally beyond the distal end of the core; and a tip cavity of the sound-attenuating body extending proximally from the tip and comprising a distal opening, the tip cavity having a volume defined by a side wall formed by the sound-attenuating body and a bottom at least partially formed by the distal end of the core. The tip cavity side wall comprising a plurality of protrusions extending inwardly toward the longitudinal axis. In some embodiments, a boss extends into the mold cavity, wherein the boss is positioned to contact the first end of the core when the first end of the core is inserted into the mold cavity. The boss may comprise a cup extending axially from a base of the mold, and a plurality of cut-outs on the cup for forming the protrusions of the tip cavity.

The above summary is not intended to describe each embodiment or every implementation of the earplugs and methods of manufacturing earplugs according to an embodiment. Rather, a more complete understanding of the invention will become apparent and appreciated by reference to the following Detailed Description and claims in view of the accompanying figures.

BRIEF DESCRIPTION OF DRAWINGS

FIG. 5A is a side view of the earplug of FIG. 1.

FIGS. 5B and 5C are cross-sectional views of the earplug of FIG. 1 taken along lines B-B and C-C, respectively, in FIG. 5A.

DETAILED DESCRIPTION

Figure 1:
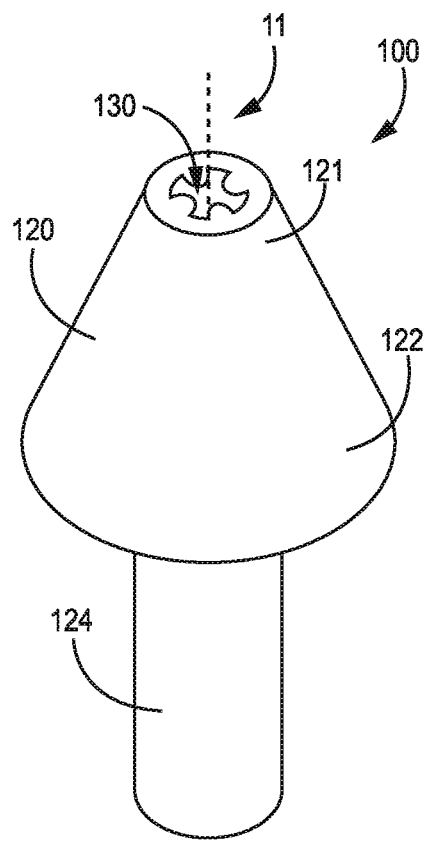
FIG. 1 is a perspective view of a push-to-fit earplug including a tip cavity according to an illustrative embodiment.
Figure 2:
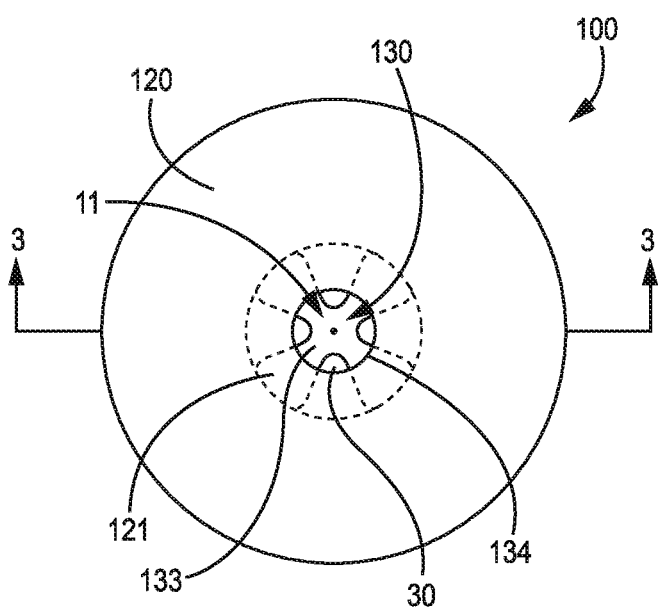
FIG. 2 is an end view of the earplug of FIG. 1 taken from the end of the earplug containing the tip cavity.
Figure 3:
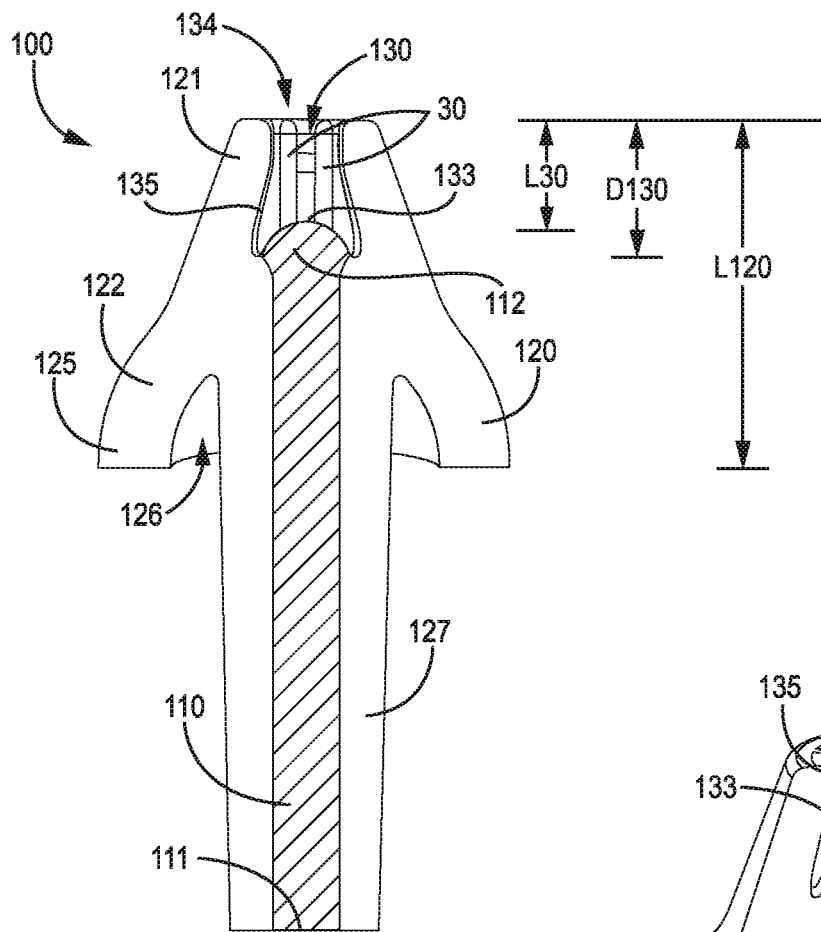
FIG. 3 is a cross-sectional view of the earplug of FIG. 1 and taken along line 3-3 in FIG. 2.
Figure 4:
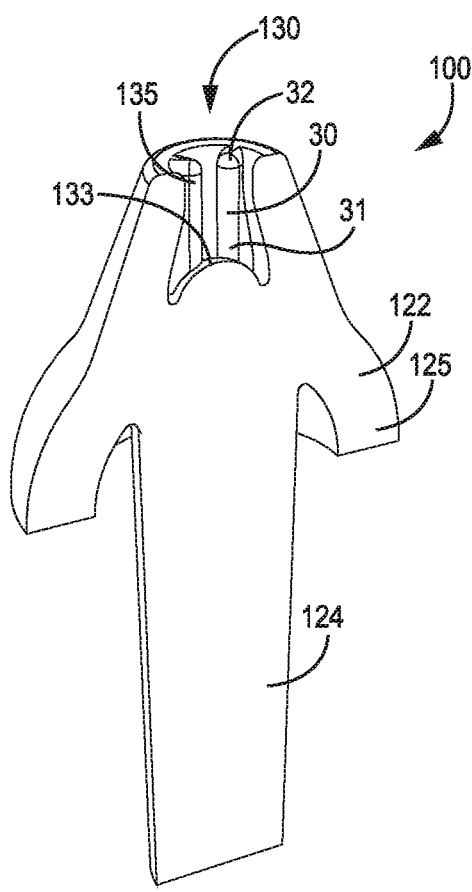
FIG. 4 is a perspective view of the earplug of FIG. 1 with a portion of the earplug cut off.
Figure 6:
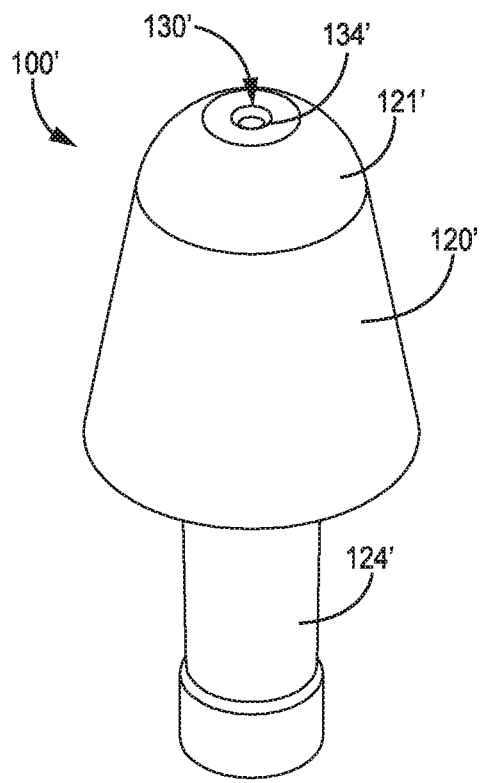
FIG. 6 is a perspective view of a push-to-fit earplug including a tip cavity according to an alternative embodiment.
Figure 7:
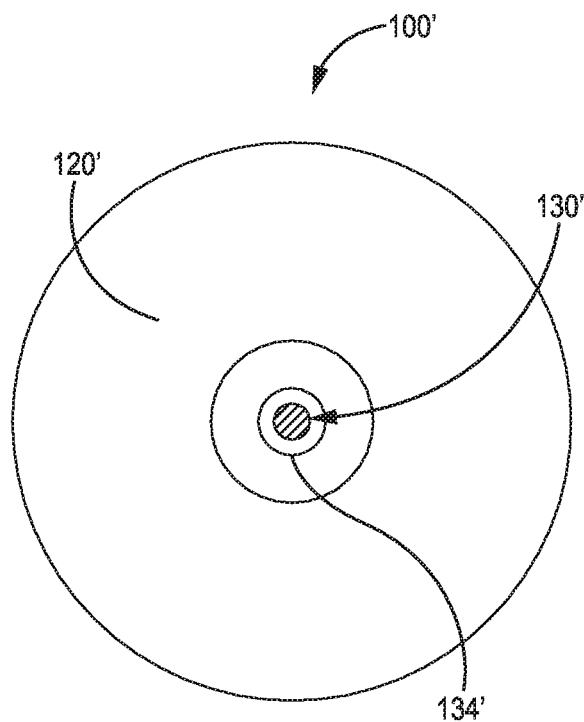
FIG. 7 is an end view of the earplug of FIG. 6 taken from the end of the earplug containing the tip cavity.
Figure 8:
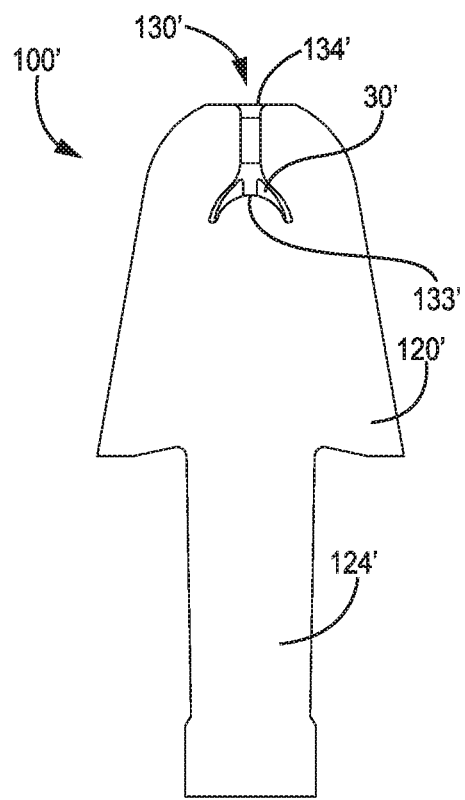
FIG. 8 is a cross-sectional view of the earplug of FIG. 6 and taken along line 7-7 in FIG. 7.
Figure 9:
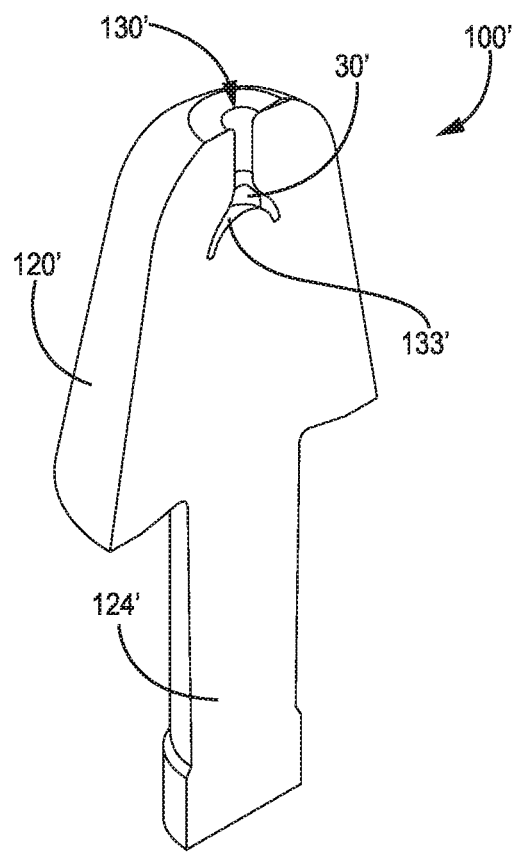
FIG. 9 is a perspective view of the earplug of FIG. 6 with a portion of the earplug cut off.

The present disclosure relates to earplugs, and more specifically to push-to-fit earplugs that include a comfort cavity (e.g., a tip cavity) at the distal tip of the earplug.

The term "mold" means a hollow form that may or may not impart a shape on a component placed in the hollow form.

The term "thermally bonded" means a state in which molecules of two materials or surfaces have diffused into the material or surface of the other when in a molten phase such that a bond is formed. Chemical bonding is absent or does not provide the primary source of bonding between thermally bonded materials or surfaces.

The term "thermoplastic" means a polymer that can be repeatedly heated and re-shaped and will retain its shape upon cooling.

As used here, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

As used here, all numbers are assumed to be modified by the term "about" and in certain situations, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

As used here, the recitations of numerical ranges by endpoints include all numbers subsumed within that range as well as the endpoints (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the invention. Thus, the appearances of such phrases in various places throughout this specification are not necessarily referring to the same embodiment of the invention. Furthermore, the particular features, configurations, compositions, or characteristics may be combined in any suitable manner in one or more embodiments.

Relative terms such as proximal, distal, left, right, forward, rearward, top, bottom, side, upper, lower, horizontal, vertical, and the like may be used in this disclosure to simplify the description, however, and not to limit the scope of the invention in any way. Terms such as left, right, forward, rearward, top, bottom, side, upper, lower, horizontal, vertical, and the like are from the perspective observed in the particular figure.

The terms "minor cross dimension" and "minor radius" are used here to refer to the smallest cross dimension/radius of an object, the smallest cross dimension/radius being the shortest length that passes through/from the center of the object in the plane where the cross dimension/radius is being measured.

The terms "major cross dimension" and "major radius" are used here to refer to a dimension of the object that is in the same plane as the minor cross dimension/radius. The major cross dimension and major radius are greater than the minor cross dimension and minor radius, respectively.

The present disclosure relates to earplugs that provide hearing protection for a user, and to methods of making earplugs. In one or more embodiments, the earplugs include a relatively stiff core covered, directly or indirectly, by a relatively soft outer layer. The outer layer forms a compressible sound-attenuating body that may be inserted into the ear canal of a user. The earplugs may also include a stem portion that may include the relatively soft outer layer over the core, with the stem portion intended to be grasped by the user during insertion and removal of the earplug. In one or more embodiments, the earplug may be inserted into an ear canal without first requiring that the sound-attenuating body be compressed or "rolled down."

One or more embodiments of methods of making earplugs are also described. In one or more embodiments, the methods may reduce the difficulty and/or the cost of manufacturing earplugs. The methods may include covering a substrate, such as a core, with an outer layer that includes an unactivated foaming agent, and activating the foaming agent such that at least a portion of the outer layer expands into a desired shape. The methods may further include using a boss or a pin during the expansion of the outer layer to form a cavity inside the tip of the earplug.

FIGS. 1-4 depict one illustrative embodiment of a push-to-fit earplug 100. The earplug 100 includes a core 110 made of a first material and having proximal and distal ends 111 and 112 (respectively). The proximal end 111 extends into the stem portion 124 of the earplug 100, and the distal end 112 extends into the sound-attenuation body 120 of the earplug 100. The earplug 100 further includes an outer layer made of a second material and bonded, directly or indirectly, to at least a portion of outer major surface of the core 110. The outer layer of second material may be used to form a sound-attenuating body 120 and may also be used to form an outer layer 127 of stem portion 124 extending from the sound-attenuating body 120.

The sound-attenuating body 120 is configured for at least partial insertion into the ear canal of a user to attenuate the passage of sound into the ear canal. Although not necessarily required, the stem portion 124 may, in one or more embodiments, have a smaller diameter than the sound-attenuating body 120. During insertion of earplug 100 into the ear canal, the stem portion 124 serves as a handle which may be gripped by a user. Earplug 100, and specifically sound-attenuating body 120, is brought proximate to the user's ear and inserted into the ear canal. Sound-attenuating body 120 compresses as it is positioned, and the core 110 provides sufficient stiffness to facilitate insertion. In use, sound-attenuating body 120 is positioned substantially within the ear canal to block the passage of sound and stem portion 124 extends outwardly from the ear canal to provide a handle for removing the earplug.

In one or more embodiments of earplugs, such as earplug 100, 100' depicted in FIGS. 1-9, the sound-attenuating body 120 includes a tip 121 and a base 122. The tip 121 of the sound-attenuating body 120 extends distally from the base 122 and the distal end 112 of the core 110. The core 110 may, in one or more embodiments (such as that depicted in FIGS. 1-9), extend into the sound-attenuating body 120.

One or more embodiments of the earplugs may include a sound-attenuating body 120 in which the base 122 of the sound-attenuating body 120 is wider than the tip 121 of the sound-attenuating body 120. Width, as used in this description, is measured in a dimension transverse to the longitudinal axis 11 that extends through the proximal end 111 and distal end 112 of the core 110.

In one or more embodiments of the earplugs, the sound-attenuating body 120 may include a flange 125 extending proximally and outwardly from the base 122 of the sound-attenuating body 120. The flange 125 may be formed by a flange cavity 126 formed in the sound-attenuating body 120. In one or more embodiments, the flange cavity 126 may be described as opening downward, away from the tip 121 of the sound-attenuating body 120. As a result, the flange 125 is essentially cantilevered from the sound-attenuating body 120.

The sound-attenuating bodies of the earplugs according to an embodiment include a tip cavity 130 that extends from the tip 121 of the sound-attenuating body 120 towards a bottom 133. The tip cavity 130 may, in one or more embodiments, provide a volume into which the surrounding material of the sound-attenuating body 120 can collapse as the earplug 100 is advanced into an ear canal and/or is resident therein. The distal end 112 of the core 110 is recessed into the tip cavity 130 which may reduce the likelihood that a user will feel the distal end 112 of the core as the sound-attenuating body 120 is inserted into and/or resident within an ear canal. In one or more embodiments, all or a portion of the distal end 112 of the core 110 may be exposed within the tip cavity 130. In one or more alternative embodiments, the distal end 112 of the core 110 may be partially or completely covered by a layer of the material used to form the sound-attenuating body 120.

Although the illustrative embodiment of tip cavity 130 and a distal end 112 of core 110 are depicted as having circular cross-sectional shapes (as seen in, e.g., FIG. 2), in one or more alternative embodiments, the tip cavities and/or proximal ends of the cores used in earplugs according to an embodiment may have any suitable shape, e.g., hexagonal, pentagonal, octagonal, triangular, square, etc.

The tip cavity 130 has a depth D130 and a volume V130, defined by a side wall 135 formed by the sound-attenuating body and the bottom 133 that may be at least partially formed by the distal end 112 of the core 110. According to an embodiment, the tip cavity side wall 135 defines a plurality of protrusions 30 extending inwardly toward the center of the tip cavity (toward the longitudinal axis 11), as shown in FIGS. 1-9.

Although the figures depict an embodiment with four protrusions 30, the tip cavity 130 may include any suitable number of protrusions 30, including odd and even numbers, such as from 2 to 12, from 3 to 10, or from 4 to 8 protrusions 30.

The protrusions 30 have a proximal end 31 and a distal end 32, with the proximal end 31 disposed at or adjacent the bottom 133 of the tip cavity 130, and a length L30 extending between the proximal and distal ends 31, 32. The protrusions 30 may define pillars such that the length of each pillar extends in a plane with the longitudinal axis 11. The protrusion 30 may be angled inward such that the distal ends 32 of the protrusions 30 may be closer together than the proximal ends 31.

The plurality of protrusions 30 may be integrally formed with the sound-attenuating body 120, and may form a portion of the sound-attenuating body 120. In some embodiments, the protrusions 30 extend distally from the bottom 133 of the tip cavity 130. For example, the proximal ends 31 of the protrusions 30 may contact the distal end 112 of the core 110. The proximal end 31 of each protrusion 30 may be thermally bonded to the distal end 112 of the core 110. The proximal end 31 of each protrusion 30 may also be bonded chemically (e.g., by covalent bonds) or by surface bonding (e.g., by dipolar interactions, van der Waals forces, or hydrogen bonding) to the distal end 112 of the core 110.

When viewed in a cross-sectional plane perpendicular to the longitudinal axis 11 (see FIGS. 5A-5C), the tip cavity 130 has a first cross-sectional area A131 at a first cross-sectional plane (FIG. 5B) and a second cross sectional area A132 at a second cross-sectional plane (FIG. 5C). The first cross-sectional plane is taken along a line at or adjacent the distal end 112 of the core 110 which may form at least a part of the bottom 133 of the tip cavity 130. The second cross-sectional plane is taken along a line at or adjacent the distal opening 134 of the tip cavity 130.

Referring now to FIG. 5B, the tip cavity 130 has a minor radius R33 that extends from the center of the tip cavity 130 (the longitudinal axis 11) to the apex 33 of a protrusion 30 in the first cross-sectional plane. The tip cavity 130 also has a major radius R135 that extends from the center to the wall 135 between two adjacent protrusions 30. The tip cavity 130 also has a first major cross dimension D131 determined as the largest cross dimension of the tip cavity in the plane. For example, in some embodiments (e.g., where there are an even number of protrusions), the first major cross dimension D131 may be determined as two times the major radius R135. In some embodiments, the minor radius R33 is from about 15 to about 85%, from about 20 to about 75%, or from about 25 to about 65% of the major radius R135.

At the second cross-sectional plane, shown in FIG. 5C, the tip cavity 130 has a second major cross dimension D132, determined as the largest cross dimension of the tip cavity 130 in that plane. In some embodiments, the first major cross dimension D131 is greater than the second major cross dimension D132. For example, the second major cross dimension D132 may be from about 5 to about 80%, from about 10 to about 60%, or from about 20 to about 50% of the first major cross dimension D131.

The distal end 112 of the core 110, which may form a portion of the bottom 133 of the tip cavity 130, has a cross dimension D112. For example, the distal end 112 of the core 110 may form a first portion of the bottom 133 of the tip cavity 130, and the sound-attenuating portion 120 may form a second portion of the bottom 133. A portion or all of the distal end 112 of the core may be exposed (e.g., visible) at the bottom 133 of the tip cavity 130. Further, the distal end 112 of the core may extend distally beyond the second portion of the bottom 133 formed by the sound-attenuating portion 120. Further, the distal end 112 of the core 110 may have a non-planar distal surface, such as a convex, curved surface. The core 110 has a cross-section that may be uniform at any location between the proximal end 111 and the distal end 112 of the core 110, or may vary along the length of the core 110 (e.g., be narrower at one end than the other).

In some embodiments, the cross dimension D112 of the distal end 112 of the core 110 is smaller than the first major cross dimension D131 of the tip cavity 130. For example, the cross dimension D112 may be about 50% or more of the first major cross dimension D131, or about 70% or more, about 80% or more, or about 90% or more of the first major cross dimension D131. In some embodiments, the cross dimension D112 may be up to 100%, up to 110%, or up to 120% of the first major cross dimension D131. The cross dimension D112 of the distal end 112 of the core 110 may also be greater than the second major cross dimension D132 of the tip cavity 130 (i.e., greater than the size of the distal opening of the tip cavity 130).

The tip cavity 130 has a depth D130 extending parallel to the longitudinal axis 11 from the proximal-most point of the bottom 133 to the distal opening 134. The depth D130 may range from about 2.5 to about 10 mm, from about 3.8 to about 8.3 mm, or from about 4.7 to about 6.3 mm. The sound-attenuating body 120 has an axial length L120, and the depth D130 of the tip cavity 130 may range from about 10 to about 65%, from about 20 to about 60%, or from about 30 to about 50% of the axial length L120 of the sound-attenuating body 120.

The sound-attenuating body 120 has a volume that is defined as a volume occupied by the material that makes up the sound-attenuating body 120. In some embodiments, the tip cavity 130 has a volume V130 that is from about 1 to about 10%, from about 2 to about 7, or from about 3 to about 5% of the volume of the sound-attenuating body 120.

In some embodiments, the protrusions 30 disposed in the tip cavity 130 have a length L30 that extends from the bottom 133 of the tip cavity 130 to the distal opening 134 of the tip cavity 130. The plurality of protrusions 130 may be visible through the distal opening 134 of the tip cavity 130. In an alternative embodiment, shown in FIGS. 6-9, the protrusions 30' extend only part of the way toward the distal opening 134, having a length L30' that is shorter than the depth D130 of the tip cavity 130. For example, in the alternative embodiment, shown in FIGS. 6-9, the length L30' may be from about 14 to about 95%, from about 16 to about 80%, from about 18 to about 60%, or from about 20 to about 50% of the depth D130 of the tip cavity 130.

According to an embodiment, the protrusions 30 occupy a volume within the tip cavity 130. If compared to the same tip cavity without protrusions, the plurality of protrusions 30 occupies from about 5 to about 60%, from about 7 to about 55%, from about 15 to about 55%, or from about 25 to about 60% of the volume of the tip cavity 130 measured without the plurality of protrusions. The tip cavity volume measured without the plurality of protrusions may range from about 0.02 cm$^3$ to about 0.2 cm$^3$, or from about 0.04 cm$^3$ to about 0.1 cm$^3$.

The specific outer shape of the sound-attenuating body 120 is not particularly limited, and the illustrative embodiments depicted in FIGS. 1-9 are only examples of potentially suitable shapes for an earplug in accordance with the present disclosure. For example, the shape of the sound-attenuating body 120 could be more or less pointed, or more or less rounded, and the sides of the outer surface of the sound-attenuating body 120 could be more or less angled.

Figure 15:
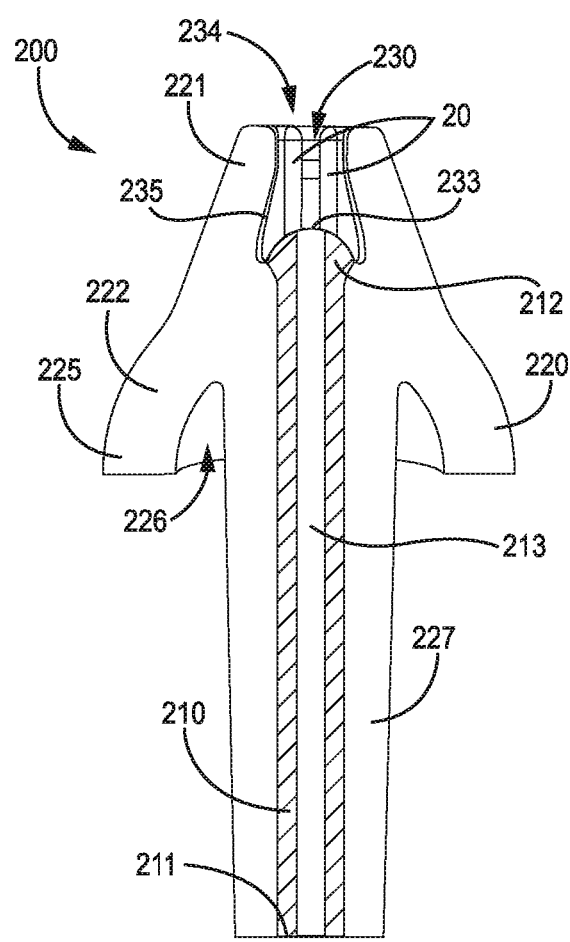
FIG. 15 is a cross-sectional view of a push-to-fit earplug including a tip cavity according to an alternative embodiment.

Another variation of the earplug 200 shown in FIG. 15 is that the core 210 includes a channel 213 that extends through the core 210 between the proximal end 211 and the distal end 212. The core 210 may be surrounded by an outer layer 227, which may include the same material as the sound-attenuating body 220. The channel 213 may extend through the bottom 233 of the tip cavity 230 and be open into the tip cavity 230. The protrusions 20 and the channel 213 may be sized and positioned such that the protrusions 20 contact the core material surrounding the channel 213 at the distal end 212. The earplug 200 may otherwise be similar to the embodiments discussed above, including a sound-attenuating body 220 with a tip 221 and a base 222, and optionally a flange 225 and flange cavity 226. Earplugs according to an embodiment that include channels passing through the earplug may be manufactured such that components of a receiver or of a communication system may be attached to the earplug. Alternatively, or in addition, a channel (such as, e.g., channel 213) may accommodate one or more filters or other passive hearing elements to provide an attenuation curve having a desired shape. For example, filters positioned in channel 213 may cause nonlinear attenuation of high level impulses produced by explosions, gunfire, or the like Channels provided in one or more embodiments of earplugs according to an embodiment may also provide a recess that a cord may be attached to, such that first and second earplugs may be joined, or that ends of a headband may be attached to in a semi-aural hearing protector.

The core 110 and the sound-attenuating body 120 may be constructed from any suitable materials. The core 110 may be constructed of a first material and the sound-attenuating body 120 may be constructed of a second material. The second material may be different from the first material, and/or may have a degree of foaming that is different from the first material.

The core material may be selected to provide a substrate onto which an outer layer of material may be provided and that may facilitate insertion of earplugs into the ear canal of a user. In the illustrative embodiment depicted in FIGS. 1-9, core 110 is made of a first material that exhibits greater rigidity or stiffness than the second material used to form the sound-attenuating body 120 (and, in the depicted embodiment, an outer layer 127 of the stem portion 124), yet is soft enough to be comfortable and safe for a user. In one or more embodiments, the first material of the core 110 may be different than the material used to form the sound-attenuating body 120 and the outer layer 127 of the stem portion 124. In one or more alternative embodiments, the first material of the core 110 may be the same material chemically, but may be formed or provided in a manner that results in different stiffness between the first material and the second material (e.g., by virtue of density, hardness, etc.).

The core material may provide a sufficiently stiff stem portion 124 so that earplug 100 may be positioned at least partially in the ear of a user without the need to first compress or "roll down" sound-attenuating body 120. In one or more embodiments, the core 110 may also exhibit an appropriate level of flexibility such that it may slightly deform to follow the contours of the ear canal when positioned there.

The core 110 may be made from one or more materials that can suitably bond to, and are otherwise compatible with, the material used to form the sound-attenuating body 120. In one or more embodiments, core 110 is made from a first material that includes thermoplastics. Suitable exemplary materials include homopolymers and copolymers of polypropylene, and blends of polypropylene and styrene-ethylene-butylene-styrene (SEBS), such as TUFPRENE™ available from S&E Specialty Polymers, LLC of Lunenburg, Mass. Other potentially suitable materials include SANTOPRENE™ 101-90, available from Exxon Mobil Corporation in Irving, Tex., and other materials exhibiting appropriate stiffness such that the sound-attenuating body 120 of earplug 100 may be easily inserted into the ear canal of a user.

The core material may be selected such that the core 110 exhibits a desired stiffness. For example, the material can be selected to have a specified flexural modulus. In certain embodiments, at least a portion of the core 110 has flexural modulus from about 0.3 to about 4 GPa. A desired hardness may depend on the dimensions of core 110 such that the core 110 exhibits a desired stiffness. Although the illustrative embodiment of core 110 shows only a single material, one or more alternative embodiments of cores used in earplugs according to an embodiment may include multiple layers to provide one or more desired characteristics.

The sound-attenuating body 120 may be constructed of a second material that may include a cellular material (e.g., a foam) that includes a plurality of cells formed or contained within the material. The same material may also form an outer layer of the stem portion of the earplug according to an embodiment. The cells may contain a gas (e.g., air) and may be formed by any suitable process.

The second material may be a soft and pliable foam, rubber, polymer, or other suitable material that may be comfortably positioned in an ear canal of a user. In some embodiments, the second material is initially a pre-mixture of material that during the making of the earplug is foamed to form the sound-attenuating body. The same material may also form a portion (e.g., an outer layer) of the stem. The stem portion may be foamed to a lesser degree (i.e., higher density), or may not be foamed at all. Examples of suitable materials for the second material include thermoplastics, thermoplastic elastomers, partial thermosets, thermoset polymers, and combinations thereof. For example, the second material may include styrene-ethylene-butylene-styrenes (SEBS), such as MONPRENE MP 1900 available from Teknor Apex of Pawtucket, R.I. Other suitable materials include plasticized polyvinyl chloride, ethylene propylene diene monomer (EPDM) rubber, styrene butadiene rubber (SBR), butyl rubber, natural rubbers, other thermoplastics, thermoset polymers, and other suitable materials as known in the art that can be formulated to exhibit an appropriate hardness range.

In one or more embodiments, the first and second materials may be selected such that the primary source of bonding between the core and material used for the sound-attenuating body (directly or indirectly) is thermal bonding. For example, in one embodiment the sound-attenuating body is thermally bonded to the outer surface of the core or the stem. In one or more embodiments, an additional adhesive is not required to bond the core to the sound-attenuating body and, as a result, an adhesive is not present between core and the sound-attenuating body. In some embodiments, the earplug is free of adhesives. Although the sound-attenuating bodies of earplugs may be described as being constructed of a second material, in one or more embodiments the sound-attenuating bodies may be constructed of multiple layers of the same or different materials (which may, e.g., be arranged concentrically). For example, a first layer may be used to provide desired characteristics for contacting an ear canal of a user and a second layer may be used to facilitate a robust bond with the core, while one or more additional layers may be used to provide other desired characteristics.

The second material used in the sound-attenuating body may be selected to control the friability of the outer surface of the sound-attenuating body such that it may not easily be broken or disintegrate during use. The friability of an earplug may be controlled in part by selecting a material having an appropriate molecular weight, with higher molecular weight generally resulting in a less friable earplug. In an exemplary embodiment, an outer layer of the sound-attenuating body includes an SEBS having a molecular weight between 100,000 Daltons and 200,000 Daltons, as measured by gel permeation chromatography analysis as known in the art, such as according to ASTM D6474-99.

The density of the second material (e.g., an outer layer of the sound-attenuating body) can be controlled during manufacturing to provide a specified density as desired for a particular application. The second material may, for example, exhibit a density that varies by thickness such that the second material used in the sound-attenuating body has an integral outer skin that is denser than the second material located closer to the core. Such a skin may be present on one or both of sound-attenuating body and the stem portion (where the stem portion includes, for example, a layer of the second material used in the sound-attenuating body). Alternatively, the second material may have a substantially uniform density.

In one or more embodiments in which the stem portion includes a layer of the second material used in the sound-attenuating body and, the second material of the sound-attenuating body may have a first average density $\rho 1$ and the second material in the outer layer of the stem portion may have a second average density $\rho 2$. First and second average densities ρ1 and ρ2 can be found by averaging the densities at each location of sound-attenuating body or outer layer of stem portion. Without being bound by theory, the average density is believed to provide an indication of the ability of sound-attenuating body or outer layer of stem portion to compress or otherwise conform when subjected to an external force. The first average density ρ1 of a sound-attenuating body may, in one or more embodiments, be selected such that a sound-attenuating body may provide a comfortable fit by conforming to the ear canal of a user, while providing a desired level of sound attenuation. In various illustrative embodiments, the first average density ρ1 of the second material in a sound-attenuating body, comprising a foamed SEBS for example, is between 100 kg/m$^3$ and 300 kg/m$^3$, 150 kg/m$^3$ and 250 kg/m$^3$, or may be about 200 kg/m$^3$. The second average density ρ2 of the second material in the outer layer of stem portion may be greater than the first average density ρ1, and in various illustrative embodiments is between 200 kg/m$^3$ and 400 kg/m$^3$, between 250 kg/m$^3$ and 350 kg/m$^3$, or may be about 300 kg/m$^3$.

Figure 10:
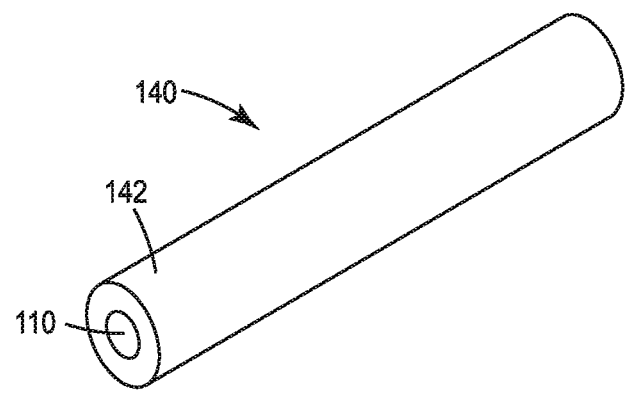
FIG. 10 is a perspective view of one illustrative embodiment of a pre-form that includes a core and an outer layer in an intermediate state of one illustrative embodiment of a method of making an earplug according to an embodiment.

One or more embodiments of the earplugs according to an embodiment may be formed in a multiple step process. In one or more embodiments, the earplugs described herein may be formed in a process that involves an intermediate state in which a core is covered with an outer layer of a second material (directly or indirectly), to result in a pre-formed hearing protection device that may be referred to as a pre-form, but which does not yet include a sound-attenuating body. One illustrative embodiment of a pre-form is depicted in FIG. 10. The pre-form 140 includes an outer layer 142 located over a core 110. In one or more embodiments, the outer layer 142 of pre-form 140 includes an unactivated foaming agent. In one or more embodiments, the unactivated foaming agent includes an expandable sphere foaming agent that includes thermoplastic spheres, for example, that include a shell encapsulating a hydrocarbon or other appropriate gas that expands when exposed to heat or other activation source. Expansion of the thermoplastic shell results in an increased volume and reduced density of the material of outer layer 142. The unactivated foaming agent may also be a chemical foaming agent that includes an expandable material that is self-contained or otherwise not contained by an expandable sphere. Activation of such a foaming agent causes the expandable material to expand creating voids or gaps in the material of the outer layer.

Activation of the foaming agent or agents present in outer layer 142, and the associated expansion of outer layer 142, can be controlled to provide an earplug having a sound-attenuating body and outer layer of stem portion exhibiting a desired shape, density, hardness, and other desired characteristics. The presence of both an expandable sphere foaming agent and a chemical foaming agent may assist in providing sufficient structure and expansion such that the outer layer may be appropriately formed during activation, while reducing the hardness of the outer layer from a level that would otherwise result if only an expandable sphere foaming agent were used. Some or all of a gas generated by a chemical foaming agent may escape during activation such that some or all of the gas is not present in the outer layer after activation. Some or all of an expandable sphere foaming agent may remain in the outer layer of a final earplug such that a final earplug may include thermoplastic spheres. In one or more illustrative embodiments, the material used in outer layer 142 which forms the sound-attenuating bodies and an outer layer of the stem portions of earplugs according to an embodiment may include between 1% and 10% by weight of the foaming agent or remnants of the foaming agent after being formed into the sound-attenuating body and the outer layer of the stem portion.

In the intermediate state shown in FIG. 10, pre-form 140 may have a length that is roughly equivalent to the desired length of an earplug to be formed from the pre-form 140. In one or more alternative embodiments, the pre-form 140 may have an extended length that is sufficient for subsequent formation of two or more earplugs. Pre-form 140 having an extended length may facilitate handling for subsequent processing and activation of the foaming agent. In one or more embodiments, pre-form 140 is cut to an extended length that can be subsequently cut and activated to yield a desired quantity of earplugs. An extended pre-form 140 may be coiled or otherwise shaped for ease in transporting or handling.

Methods of making personal protective equipment, such as earplugs according to an embodiment, may include covering a core with an outer layer, and applying heat to at least a portion of the outer layer such that at least a portion of the outer layer expands to form a sound-attenuating body and, in one or more embodiments, an outer layer of a stem portion. Expansion of the outer layer may, in one or more embodiments, occur due to activation of a foaming agent present in the material of the outer layer and can be controlled by positioning at least a portion of the outer layer in a mold prior to expansion. Portions of the outer layer may be confined by the shape of the mold as the outer layer expands, or are shielded from heat to limit activation of the foaming agent.

Figure 11:
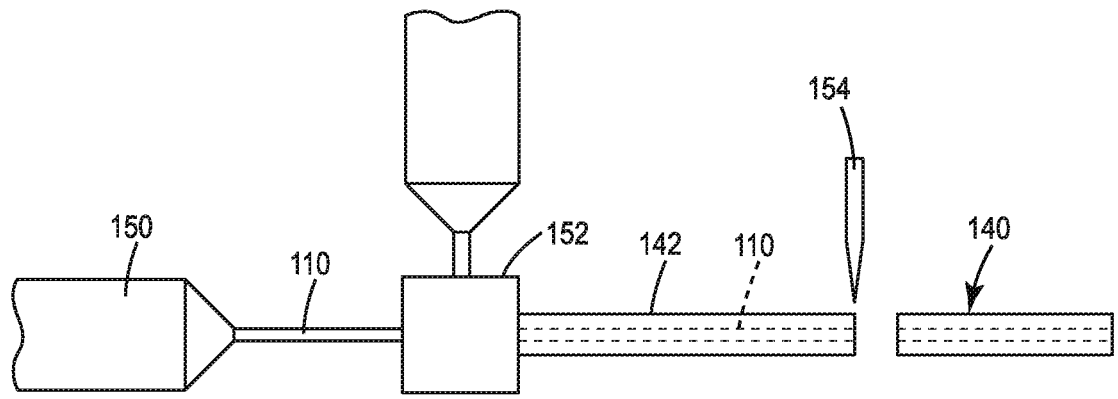
FIG. 11 is a schematic representation of one illustrative embodiment of a manufacturing process according to an embodiment.

A schematic diagram of one illustrative embodiment of a process of making earplugs according to an embodiment is depicted in FIG. 11. In the depicted process, an extended core 110 is formed by extruding a first material through a first die 150 and drawing the first material to an appropriate diameter. As described above, the core may be solid or may include a longitudinal channel extending through all or a portion of core 110, and may include one or more concentric layers having differing characteristics. The first material may be cooled such that it remains stable in subsequent steps of the manufacturing process. The magnitude of temperature change may depend on the materials used and the desired characteristics of the final product. In one or more embodiments, elongate core 110 is cooled as necessary such that it exhibits a temperature at a point before being covered by second die 152 that is lower than an activation or curing temperature of the second material used for outer layer 142. Prior to being covered by the second material of outer layer 142, elongate core 110 has an extended length and is not yet cut to the desired length for an earplug.

In the embodiment shown in FIG. 11, elongate core 110 is covered, directly or indirectly, with an outer layer 142 comprising a second material by second die 152. Second die 152 may be a co-extrusion die or other suitable die as known in the art. In one or more embodiments, the second material includes a thermoplastic and one or more unactivated foaming agents. Outer layer 142 is applied to elongate core 110 while remaining at a temperature below an activation temperature of the unactivated foaming agents. In one or more embodiments, the second material includes SEBS and a foaming agent having an activation temperature between 100 and 205° C. Other suitable materials may include plasticized polyvinyl chloride, ethylene propylene diene monomer (EPDM) rubber, styrene butadiene rubber (SBR), butyl rubber, natural rubbers, other thermoplastics, thermoset polymers, and other suitable materials as known in the art. In embodiments in which outer layer 142 includes a second material having a rubber or thermoset polymer, outer layer 142 may be applied at a temperature below a vulcanizing or curing temperature of the rubber or thermoset polymer. In such an embodiment, outer layer 142 may include an unactivated foaming agent and an uncured or partially cured rubber or thermoset polymer that can be subsequently activated and cured, respectively, with heat or other suitable activation or curing process.

In one or more embodiments, outer layer 142 is in a molten state when applied to cover core 110. As a result, molecules of outer layer 142 and core 110, or of one or more intermediate layers, are believed to diffuse into the material or surface of each other and a thermal bond is formed. The core 110 may be covered with outer layer 142, or one or more intermediate layers, by laminating, molding, spraying, dipping, or other suitable process as known in the art as an alternative or in addition to second die 250. Such steps may occur before or after core 110 is cut to a desired length. Regardless of the process used, the temperature of outer layer 142 should remain below the activation temperature of the foaming agent(s) such that the foaming agent(s) remain unactivated during the covering process.

In one or more embodiments, core 110 covered by outer layer 142 is cut to the length of a desired earplug with cutter 154. The result is pre-form 140 having core 110 and outer layer 142 in which outer layer 142 includes an unactivated foaming agent that may be subsequently activated to create an earplug having a sound-attenuating body and an outer layer of the stem portion formed by the outer layer 142 of the pre-form 140 (see, e.g., sound-attenuating body 120 and stem portion 124 of earplug 100 depicted in FIGS. 1-9).

Cutter 154 may cut pre-form 140 to a desired length of an earplug according to an embodiment, or to an extended length sufficient for subsequent formation of two or more earplugs. In one or more embodiments, pre-form 140 is cut to an extended length that can be subsequently cut and activated, or vice versa, to yield a desired quantity of earplugs. An extended pre-form 140 may be coiled or otherwise shaped for ease of handling or transportation.

In one or more embodiments, the unactivated foaming agent present in outer layer 142 includes thermoplastic spheres encapsulating a hydrocarbon or other expandable material. Application of an appropriate amount of heat causes the thermoplastic shell and hydrocarbon to expand. Expansion of outer layer 142 can be controlled by the thickness and composition of outer layer 142, selective application of heat, catalyst, or other activation source, and/or by placing at least a portion of pre-form 140 in a mold to limit expansion of outer layer 142 as the foaming agent is activated.

Figure 12A:
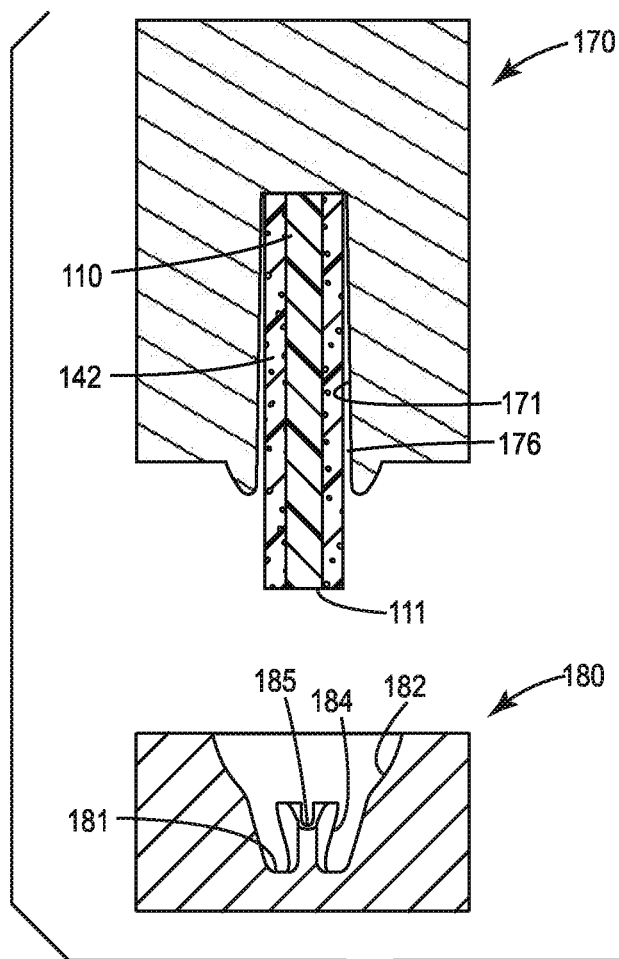
FIGS. 12A and 12B are cross-sectional views of one illustrative embodiment of a method of using a mold to manufacture an earplug according to an embodiment.
Figure 12B:
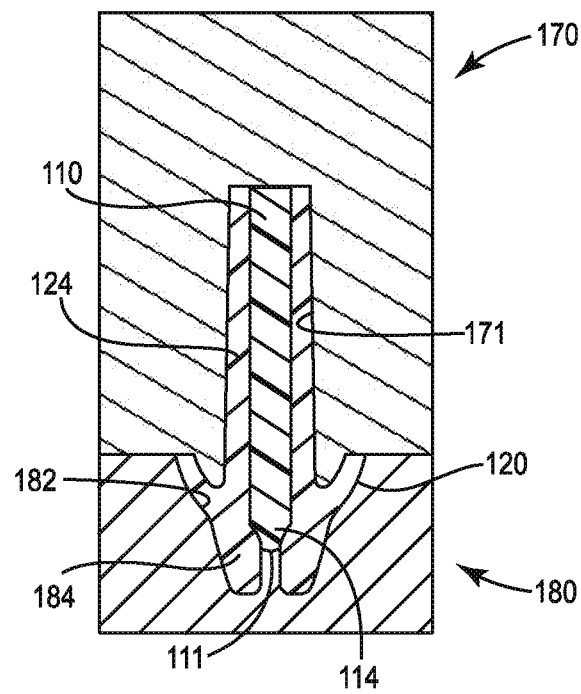

One illustrative embodiment of a mold assembly 190 that may be used to manufacture one or more embodiments of earplugs according to an embodiment is depicted in FIGS. 12A and 12B. The mold assembly 190 includes a stem portion 170 and a sound-attenuating body portion 180. The stem portion 170 and the sound-attenuating body portion 180 include, respectively, a stem cavity 171 and a sound-attenuating body cavity 182. The stem cavity 171 and the sound-attenuating body cavity 182 are used to control expansion of an outer layer of a pre-form that includes, in one or more embodiments, a core 110 and an outer layer 142. The stem cavity 171 is in the form of a stem portion that receives a portion of pre-form. The pre-forms used in mold assemblies such as the illustrative embodiment of a mold assembly 190 as depicted in FIGS. 12A and 12B, may be cut to the length of a desired earplug prior to being placed in the mold assembly 190.

Heat is applied to the pre-form located in the mold assembly 190 to raise the temperature of outer layer 142 at least to an activation temperature of a foaming agent present in outer layer 142 and cause outer layer 142 to expand as shown in FIG. 12B. In one or more embodiments, a gap 176 may exist between the outer layer 142 of the pre-form and the inner surface of the stem cavity 171. Upon application of heat or other suitable activation source, a portion of outer layer 142 expands to fill gap 176 and substantially conforms to the shape of the stem cavity 171. In one or more embodiments, the stem portion of an earplug positioned in stem cavity 171 may be effectively shielded from heat such that activation of the foaming agent is limited. Alternatively or in addition, stem cavity 171 constrains outer layer 142 and substantially inhibits expansion caused by activation of the foaming agent that would otherwise result in a greater volume and less dense outer layer over the portion of the core 110 in the stem cavity 170. Due to the constraint of the mold and/or limited activation of the foaming agent, the stem portion of an earplug (see, e.g., stem portion 124 in earplug 100 as depicted in FIGS. 1-9) may have a greater average density and/or a greater hardness than that of sound-attenuating body portion of the same earplug.

The illustrative mold assembly 190 includes a sound-attenuating body cavity 182 that is used to provide the shape of a sound-attenuating body of an earplug according to an embodiment. When a portion of pre-form is initially placed in the sound-attenuating body cavity 182, the portion of the pre-form in the sound-attenuating body cavity 182 does not occupy all of the cavity 182. As the material in outer layer 142 is heated it may be softened and a foaming agent in the outer layer 142 is activated, causing the material of the outer layer to expand to fill the sound-attenuating body cavity 182. In one or more embodiments, some of the material in the portion of the outer layer 142 located in the stem cavity 171 may flow into the sound-attenuating body cavity 182. In one or more embodiments, the mold assembly may include one or more small gas vents to allow excess gas to escape while preventing passage of any molten material as the material in the outer layer 142 expands.

The mold assembly may be oriented such that the stem cavity 171 is positioned above the sound-attenuating body cavity 182. In such an orientation, any flow of material from the stem cavity 171 into the sound-attenuating body cavity 182 during the expansion process may be enhanced. In one or more embodiments, such an orientation may facilitate the formation of an integral skin on sound-attenuating body of an earplug formed using the mold assembly because cells or gaps formed during activation of the foaming agent may tend to move upward and away from a lower surface of the sound-attenuating body cavity 182.

In addition to forming the outer shape of the sound-attenuating body of an earplug according to an embodiment, the sound-attenuating body cavity 182 also includes a boss 184 that extends upward toward the opening of the sound-attenuating body cavity 182, i.e., extends towards the stem cavity 171 of the mold assembly 190. The boss 184 can be described as extending upwards from a bottom 181 of the cavity 182. The boss 184 is used, in one or more embodiments, to form the tip cavity 130 in the sound-attenuating body 120.

The boss 184 may include a depression 185 that is positioned to receive the distal end 111 of the core 110 of the pre-form and, in some embodiments, to deform the distal end 112. The deformation of the distal end 112 of the core 110 may produce an enlarged portion at the distal end 112.

That deformation of the distal end 112 of the core 110 may be caused by the application of heat and/or pressure by the depression 185 of boss 184.

Figure 13:
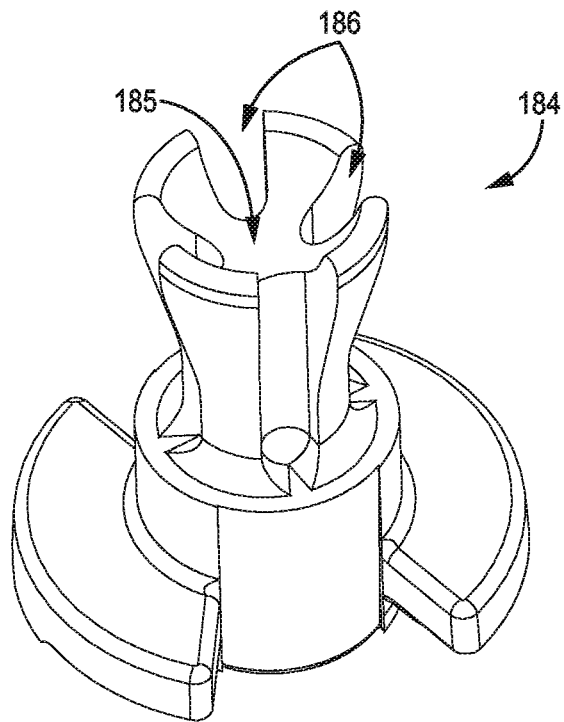
FIG. 13 is a perspective view of a mold piece for making the earplug of FIG. 1.
Figure 14:
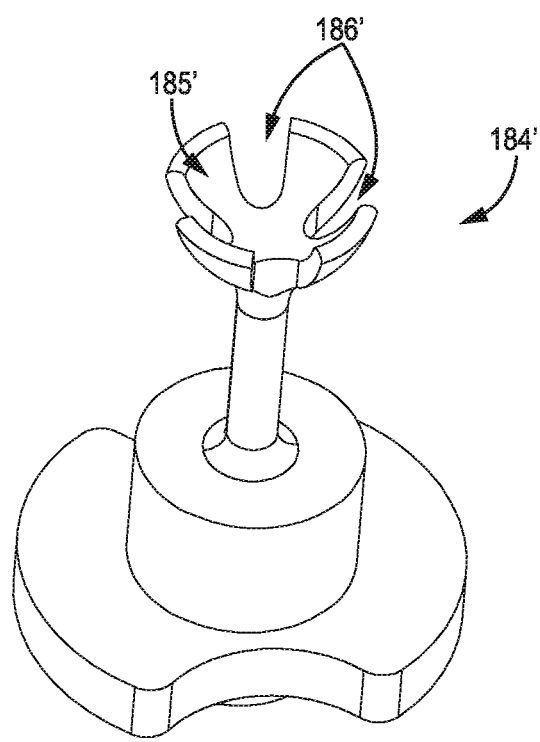
FIG. 14 is a perspective view of a mold piece for making the earplug of FIG. 6.

The boss 184 further includes a plurality of cut-outs 186 that form the protrusions 30 in the tip cavity 130. The number, shape, and size of the cut-outs 186 mirror the intended shape and size of the protrusions 30 discussed above. For example, the cut-outs 186 have a length that may extend the height of the boss 184 for creating protrusions 30 that extend from the bottom 133 of the tip cavity 130 to the distal opening 134 of the tip cavity 130, as shown in FIGS. 1-4 (protrusions 30) and FIG. 13 (boss 184). On the other hand, the length of the cut-outs 186' may extend only a part of the height of the boss 184' for creating protrusions 30' that extend only part of the way from the bottom 133 toward the distal opening 134 of the tip cavity 130, as shown in FIGS. 6-9 (protrusions 30') and FIG. 14 (boss 184'). The boss 184 may include, for example, 2 to 12, 2 to 10, 3 to 8, or 4 to 6 cut-outs 186, 186'.

After expansion of the outer layer 142 such that the material occupies all of the stem cavity 171 and the sound-attenuating body cavity 182, the earplug thus formed may be cooled and ejected from the mold assembly. The earplug thus formed includes a sound-attenuating body 120 having the shape of the sound-attenuating body cavity 182, a tip cavity 130 having the shape of the boss 184, and a stem portion 124 having the shape of stem cavity 171.

In one or more embodiments of earplugs according to an embodiment, the earplugs may be formed from pre-forms having a total length along a longitudinal axis of between approximately 15 mm and 40 mm, or of about 25.5 mm. In one or more embodiments, the outer layer 142 of a pre-form may have an outer diameter of between approximately 2.5 mm and 7.5 mm, or of about 5.5 mm. In one or more embodiments of the pre-forms, the core may have an outer diameter of between approximately 1.5 mm and 3.5 mm, or of about 2.5 mm. In those embodiments in which the core has a channel formed therethrough, the channel may have a diameter of between approximately 1.0 mm and 2.0 mm, or of approximately 1.5 mm.

After activation of outer layer 142 of a pre-form as described above, and earplug thus manufactured may have a total length L measured along a longitudinal axis between the tip of the sound-attenuating body 120 and the opposite end of the stem portion 124 of between approximately 15 mm and 40 mm, or of approximately 25.5 mm. In one or more embodiments, sound-attenuating body 120 of earplugs according to an embodiment may have an outer diameter (measured transverse to a longitudinal axis of the earplug) at its widest point between approximately 10 mm and 20 mm, or of approximately 15 mm. In one or more embodiments, the stem portion 124 may have a diameter (measured transverse to a longitudinal axis of the earplug) of between approximately 3 mm and 10 mm, or of approximately 6.5 mm. In one or more embodiments, the core may have an outer diameter (measured transverse to a longitudinal axis of the earplug and below the bottom of the tip cavity) of between approximately 1.5 mm and 3.5 mm, or of approximately 2.5 mm. If provided in the core, a channel may have a diameter (measured transverse to a longitudinal axis of the earplug) of between approximately 1.0 mm and 2.0 mm, or of approximately 1.5 mm. The dimensions of pre-forms used to manufacture earplugs according to an embodiment and the earplugs themselves can be varied based on the materials used to form the sound-attenuating bodies and/or the cores.

The earplugs 100 described here may also be made according to variations of methods described herein and other methods. For example, an earplug according to an embodiment may be made by covering a relatively stiffer elongate core with an outer layer as a foaming agent is activated, or covering a relatively stiffer elongate core with an outer layer that has been previously foamed. The foamed outer layer may be subsequently cut, compressed, densified, or otherwise shaped to form an outer layer having a stem portion and a sound-attenuating body having a tip cavity located therein.

Although the illustrative embodiments of earplugs described herein include a sound-attenuating body that is made of material that is also used and integrally formed with at least the outer layer of a stem portion, one or more alternative embodiments of the earplugs according to an embodiment can be made by any suitable technique. In one or more alternative embodiments, an earplug according to an embodiment could be manufactured in a plurality of pieces that are then assembled and/or attached to each other to form a complete earplug. For example, a sound-attenuating body and a stem portion may be separately constructed and then assembled together and attached by any suitable technique or combination of attachments, e.g., welds (sonic, thermal, chemical, etc.), adhesive, an interference fit, mechanical connections (threaded connection, mechanical fasteners, etc.).

U.S. Pat. No. 8,968,613 (Endle et al.), titled Method of Making an Earplug and U.S. Pat. No. 9,549,855 (Hamer et al.), describe methods of making personal protective equipment such as a push-to-fit earplug and materials used in those methods that may be used in part and/or with some modifications to manufacture earplugs according to an embodiment.

The earplugs and methods of making earplugs according to an embodiment may, in one or more embodiments, provide one or more benefits. In one or more embodiments, the earplugs described herein may be comfortably positioned in the ear canal of a user to provide a desired level of hearing protection, and the presence of a stiffer elongate core in the earplug may promote hygiene and/or reduce insertion time by eliminating the need to roll down a sound-attenuating body prior to insertion. The presence of a tip cavity may, in one or more embodiments, allow one or more portions of a sound-attenuating body surrounding the tip cavity to collapse inward upon insertion, thus possibly enhancing the ability of the earplugs described herein to conform to the ear canal of a user. The presence of a plurality of protrusions in the tip cavity may, in one or more embodiments, lessen the likelihood that a user can feel the stiff core disposed inside the sound-attenuating body.

EXEMPLARY EMBODIMENTS

Embodiment 1 is an earplug comprising:
a core comprising a proximal end, a distal end, and a major outer surface and a longitudinal axis extending from the proximal end to the distal end;
a sound-attenuating body attached to the major outer surface of the core, the sound-attenuating body comprising a base and a tip, the distal end of the core disposed within the sound-attenuating body and the tip extending distally beyond the distal end of the core; and
a tip cavity of the sound-attenuating body extending proximally from the tip and comprising a distal opening, the tip cavity having a volume defined by a side wall formed by the sound-attenuating body and a bottom at least partially formed by the distal end of the core, the tip cavity side wall comprising a plurality of protrusions extending inwardly toward the longitudinal axis.

Embodiment 2 is the earplug of embodiment 1, wherein the plurality of protrusions comprises from 2 to 12, from 3 to 10, or from 4 to 8 protrusions.

Embodiment 3 is the earplug of embodiment 1 or 2, wherein the plurality of protrusions comprises from 3 to 6 protrusions.

Embodiment 4 is the earplug of any of the above embodiments, wherein each of the of protrusions has a proximal end that contacts the distal end of the core.

Embodiment 5 is the earplug of embodiment 1, wherein each of the plurality of protrusions is thermally bonded to the distal end of the core.

Embodiment 6 is the earplug of any of the above embodiments, wherein the plurality of protrusions is integrally formed with the sound-attenuating body.

Embodiment 7 is the earplug of any of the above embodiments, wherein each of the plurality of protrusions extends distally from the bottom of the tip cavity.

Embodiment 8 is the earplug of any of the above embodiments, wherein the plurality of protrusions defines pillars, each pillar individually extending in a plane with the longitudinal axis.

Embodiment 9 is the earplug of any of the above embodiments, wherein at a plane perpendicular to the longitudinal axis, the tip cavity has minor radius at an apex of a protrusion and a major radius between adjacent protrusions, wherein the minor radius is from about 15 to about 85%, from about 20 to about 75%, or from about 25 to about 65% of the major radius.

Embodiment 10 is the earplug of any of the above embodiments, wherein the tip cavity has a first major cross dimension at a plane at the distal end of the core and a second major cross dimension at a plane adjacent the distal opening, and wherein the first major cross dimension is greater than the second major cross dimension.

Embodiment 11 is the earplug of embodiment 10, wherein the second major cross dimension is from about 5 to about 80%, from about 10 to about 60%, or from about 20 to about 50% of the first major cross dimension.

Embodiment 12 is the earplug of embodiment 10, wherein the distal end of the core has a core cross dimension that is smaller than the first major cross dimension and greater than the second major cross dimension of the tip cavity.

Embodiment 13 is the earplug of embodiment 12, wherein the core cross dimension is from about 50 to about 120%, from about 70 to about 110%, or from about 80 to 100% of the first major cross dimension of the tip cavity.

Embodiment 14 is the earplug of any of the above embodiments, wherein a portion of the distal end of the core is exposed at the bottom of the tip cavity.

Embodiment 15 is the earplug of any of the above embodiments, wherein the distal end of the core forms a first portion of the bottom of the tip cavity and the sound-attenuating body forms a second portion of the bottom, and wherein the first portion extends distally beyond the second portion.

Embodiment 16 is the earplug of any of the above embodiments, wherein the tip cavity has a depth extending from a proximal-most point of the bottom to the distal opening, the depth ranging from about 2.5 to about 10 mm, from about 3.8 to about 8.3 mm, or from about 4.7 to about 6.3 mm.

Embodiment 17 is the earplug of any of the above embodiments, wherein the sound-attenuating body has an axial length, and the tip cavity has a depth extending from a proximal-most point of the bottom of the tip cavity to the distal opening, the depth ranging from about 10 to about 65%, from about 20 to about 60%, or from about 30 to about 50% of the axial length of the sound-attenuating body.

Embodiment 18 is the earplug of any of the above embodiments, wherein each of the plurality of protrusions has a length extending to the distal opening of the tip cavity.

Embodiment 19 is the earplug of any of the above embodiments, wherein the plurality of protrusions is visible through the distal opening of the tip cavity.

Embodiment 20 is the earplug of any of the above embodiments, wherein the distal end of the core comprises a non-planar distal surface.

Embodiment 21 is the earplug of any of the above embodiments, wherein the tip cavity has a depth extending from a proximal-most point of the bottom to the distal opening, and wherein each of the plurality of protrusions has a length extending from about 14 to about 100%, from about 15 to about 95%, from about 16 to about 80%, from about 18 to about 60%, or from about 20 to about 50% of the depth of the tip cavity.

Embodiment 22 is the earplug of any of the above embodiments, wherein the plurality of protrusions has a total volume ranging from about 5 to about 60%, from about 7 to about 55%, from about 15 to about 55%, or from about 25 to about 60% of a volume of the tip cavity measured without the plurality of protrusions.

Embodiment 23 is the earplug of any of the above embodiments, wherein the core is constructed of a first material and the sound-attenuating body is constructed of a second material, wherein the first material is different from the second material.

Embodiment 24 is the earplug of any of the above embodiments, wherein the core is constructed of a first material with a first degree of foaming and the sound-attenuating body is constructed of a second material with a second degree of foaming, wherein the first material is different from the second material.

Embodiment 25 is the earplug of any of the above embodiments, wherein the sound-attenuating body is thermally bonded to at least a portion of the outer major surface of the core.

Embodiment 26 is the earplug of any of the above embodiments, wherein the earplug is free of adhesives.

Embodiment 27 is the earplug of any of the above embodiments, wherein the core is constructed of a first material with a first degree of foaming and the sound-attenuating body is constructed of a second material with a second degree of foaming, wherein the first material is the same as the second material.

Embodiment 28 is the earplug of embodiment 23, wherein the first material comprises a thermoplastic.

Embodiment 29 is the earplug of embodiment 23, wherein the second material comprises a thermoplastic, a partial thermoset, a thermoset polymer, or a combination thereof.

Embodiment 30 is the earplug of any of the above embodiments, wherein the sound-attenuating body has a volume that is defined as a volume occupied by material that makes up the sound-attenuating body, wherein the tip cavity volume is from about 1 to about 10%, from about 2 to about 7, or from about 3 to about 5% of the volume of the sound-attenuating body.

Embodiment 31 is the earplug of any of the above embodiments, wherein the core has a cross-section that is uniform at any location between the proximal end and the distal end of the core.

Embodiment 32 is a method of making an earplug, the method comprising:
  covering at least a portion of a major outer surface of a core that comprises a first material with a second material that comprises an unactivated foaming agent, the core comprising a proximal end, a distal end, and a major outer surface and a longitudinal axis extending from the proximal end to the distal end;
  inserting the distal end of the core and at least a portion of the second material into a mold cavity; and
  activating the unactivated foaming agent in the mold cavity to form a sound-attenuating body in the mold cavity that is attached to the major outer surface of the core, the sound-attenuating body comprising:
  a base and a tip, the distal end of the core disposed within the sound-attenuating body and the tip extending distally beyond the distal end of the core; and
  a tip cavity of the sound-attenuating body extending proximally from the tip and comprising a distal opening, the tip cavity having a volume defined by a side wall formed by the sound-attenuating body and a bottom at least partially formed by the distal end of the core,
  the tip cavity side wall comprising a plurality of protrusions extending inwardly toward the longitudinal axis.

Embodiment 33 is the method of embodiment 32, wherein a boss extends into the mold cavity, wherein the boss is positioned to contact the first end of the core when the first end of the core is inserted into the mold cavity.

Embodiment 34 is the method of embodiment 33, wherein the boss comprises a cup extending axially from a base of the mold.

Embodiment 35 is the method of embodiment 34, wherein the cup comprises a plurality of cut-outs, for example 2 to 12, 2 to 10, 3 to 8, or 4 to 6 cut-outs, and wherein the second material flows into the cut-outs to form the protrusions.

Embodiment 36 is the method of embodiment 33, wherein the method further comprises deforming the distal end of the core using the boss.

Embodiment 37 is the method of any one of embodiments 32 to 36, wherein the method further comprises deforming the first end of the core in the mold cavity.

The invention claimed is:

1. An earplug comprising:
  a core comprising a proximal end, a distal end, and a major outer surface and a longitudinal axis extending from the proximal end to the distal end;
  a sound-attenuating body attached to the major outer surface of the core, the sound-attenuating body comprising a base and a tip, the distal end of the core disposed within the sound-attenuating body and the tip extending distally beyond the distal end of the core; and
  a tip cavity of the sound-attenuating body extending proximally from the tip and comprising a distal opening, the tip cavity having a volume defined by a side wall formed by the sound-attenuating body and a bottom at least partially formed by the distal end of the core, the tip cavity side wall comprising a plurality of protrusions extending inwardly toward the longitudinal axis.

2. The earplug of claim 1, wherein the plurality of protrusions comprises from 2 to 12 protrusions.

3. The earplug of claim 1, wherein the sound-attenuating body is thermally bonded to at least a portion of the outer major surface of the core; and wherein the earplug is free of adhesives.

4. The earplug of claim 1, wherein each of the plurality of protrusions has a proximal end that contacts the distal end of the core.

5. The earplug of claim 1, wherein each of the plurality of protrusions is thermally bonded to the distal end of the core; or
  wherein the plurality of protrusions is integrally formed with the sound-attenuating body.

6. The earplug of claim 1, wherein the plurality of protrusions has a total volume ranging from about 5 to about 60% of a volume of the tip cavity measured without the plurality of protrusions.

7. The earplug of claim 1, wherein each of the plurality of protrusions extends distally from the bottom of the tip cavity.

8. The earplug of claim 1, wherein the plurality of protrusions defines pillars, each pillar individually extending in a plane with the longitudinal axis.

9. The earplug of claim 1, wherein at a plane perpendicular to the longitudinal axis, the tip cavity has a minor radius at an apex of a protrusion and a major radius between adjacent protrusions, wherein the minor radius is from about 15 to about 85% of the major radius.

10. The earplug of claim 1, wherein the tip cavity has a first major cross dimension at a plane at the distal end of the core and a second major cross dimension at a plane adjacent the distal opening, and wherein the first major cross dimension is greater than the second major cross dimension.

11. The earplug of claim 1, wherein the distal end of the core comprises a non-planar distal surface.

12. The earplug of claim 1, wherein the core is constructed of a first material and the sound-attenuating body is constructed of a second material, wherein the first material is different from the second material.

13. The earplug of claim 12, wherein the first material comprises a thermoplastic; or wherein the second material comprises a thermoplastic, a partial thermoset, a thermoset polymer, or a combination thereof.

14. The earplug of claim 1, wherein a portion of the distal end of the core is exposed at the bottom of the tip cavity.

15. The earplug of claim 1, wherein each of the plurality of protrusions has a length extending to the distal opening of the tip cavity.

16. The earplug of claim 1, wherein the plurality of protrusions is visible through the distal opening of the tip cavity.

17. A method of making an earplug, the method comprising:
  covering at least a portion of a major outer surface of a core that comprises a first material with a second material that comprises an unactivated foaming agent, the core comprising a proximal end, a distal end, and wherein the major outer surface and a longitudinal axis extending from the proximal end to the distal end;
  inserting the distal end of the core and at least a portion of the second material into a mold cavity; and
  activating the unactivated foaming agent in the mold cavity to form a sound-attenuating body in the mold cavity that is attached to the major outer surface of the core, the sound-attenuating body comprising:
  a base and a tip, the distal end of the core disposed within the sound-attenuating body and the tip extending distally beyond the distal end of the core; and
  a tip cavity of the sound-attenuating body extending proximally from the tip and comprising a distal opening, the tip cavity having a volume defined by a side wall formed by the sound-attenuating body and a bottom at least partially formed by the distal end of the core, the tip cavity side wall comprising a plurality of protrusions extending inwardly toward the longitudinal axis.

18. The method of claim 17, wherein a boss extends into the mold cavity, wherein the boss is positioned to contact a first end of the core when the first end of the core is inserted into the mold cavity.

19. The method of claim 17, wherein the method further comprises deforming the first end of the core in the mold cavity.

* * * * *